United States Patent [19]

Strubbe

[11] 4,115,579
[45] Sep. 19, 1978

[54] PROCESS FOR INHIBITING BLOOD PLATELET AGGREGATION

[75] Inventor: Joseph Strubbe, Dilbeek, Belgium

[73] Assignee: U C B, Societe Anonyme, Belgium

[21] Appl. No.: 843,693

[22] Filed: Oct. 19, 1977

[30] Foreign Application Priority Data

Oct. 19, 1976 [GB] United Kingdom ............... 43300/76

[51] Int. Cl.$^2$ ............................................. A61K 31/40
[52] U.S. Cl. .................................................... 424/274
[58] Field of Search ......................................... 424/274

[56] References Cited

FOREIGN PATENT DOCUMENTS 1,039,113  8/1966  United Kingdom.
1,309,692  3/1973  United Kingdom.

*Primary Examiner*—Donald B. Moyer
*Attorney, Agent, or Firm*—Wenderoth, Lind & Ponack

[57] ABSTRACT

A process of inhibiting blood platelet aggregation, without undesirable side effects on the mechanism of coagulation, wherein an effective amount of 2-oxo-1-pyrrolidineacetamide, 2-(2-oxo-pyrrolidino)-propionamide or 2-(2-oxo-pyrrolidino)-butyramide is administered to a man requiring such inhibition. Useful in the prophylactic treatment of vascular diseases, in surgical operations and the like, to inhibit the tendency of blood platelets to aggregate.

6 Claims, 4 Drawing Figures

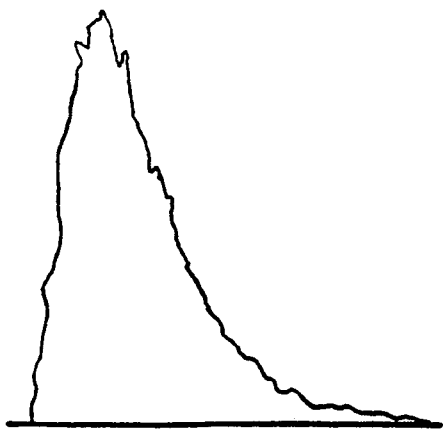
FIG. I
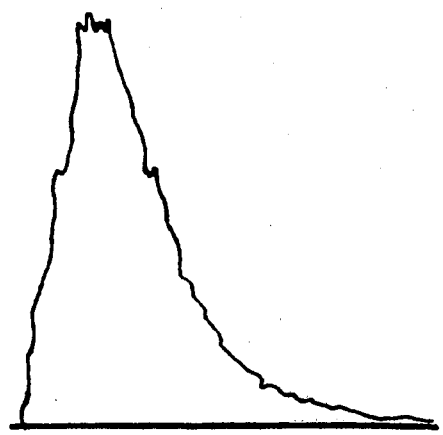
FIG. III
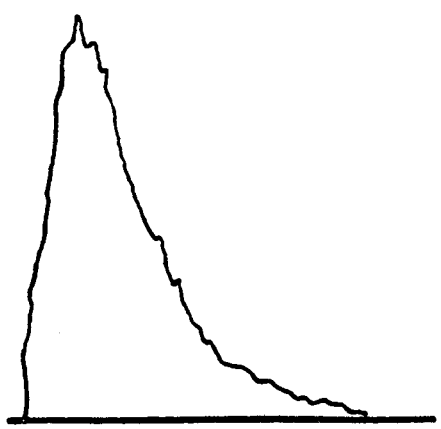
FIG. II
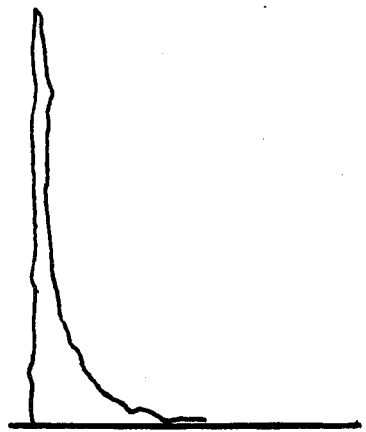
FIG. IV

PROCESS FOR INHIBITING BLOOD PLATELET AGGREGATION

The present invention relates to a pharmaceutical composition which possesses anti-aggregation and deaggregation properties with regard to blood platelets (thrombocytes). Thus, these compositions are useful for the treatment of all diseases and especially of vascular diseases, in which it is necessary to inhibit platelet aggregation or to eliminate already formed platelet aggregates. They are also useful for the prophylactic treatment of vascular diseases.

The active compounds used in these compositions are not new. The activity on the nervous system, especially the so-called nootropic activity, is already known for these compounds, which are represented by the general formula:

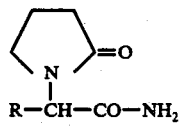
(I)

wherein R is a hydrogen atom or a methyl or ethyl radical. Thus, the following three 2-(2-oxo-pyrrolidino)-alkanamides are covered by this general formula:

compound A: 2-oxo-1-pyrrolidineacetamide (piracetam) (R = hydrogen)
compound B: 2-(2-oxo-pyrrolidino)-propionamide (R = methyl)
compound C: 2-(2-oxo-pyrrolidino)-butyramide (R = ethyl).

Compound A and the preparation thereof are described and claimed in British patent specification No. 1,039,113 and compounds B and C and the preparation thereof, are described and claimed in British patent specification No. 1,309,692, which is a Patent of Addition to the first-mentioned British patent specification.

Thus, the present invention provides a process for the treatment in man of vascular diseases, in which it is necessary to inhibit platelet aggregation or to eliminate already formed platelet aggregates by the use of an anti-aggregation agent, which comprises administering to man, as an anti-aggregation agent, a therapeutically effective dose of a compound of the above-given general formula (I).

In the course of clinical investigations carried out with these compounds in order to determine their influence on a therapy in association with indirect anti-coagulants (for example phenprocoumon), there was observed a remarkable decrease of platelet aggregation in the plasma of patients suffering from vascular diseases, without any influence, either direct or indirect, being exerted upon the anti-coagulant action of the anti-coagulants used concurrently.

These clinical observations led to an attempt to confirm this activity on the platelets by conventional methods of investigation used in this field. Indeed, compounds having such an activity are particularly desirable but hitherto it has not been possible to find compounds which are satisfactory from all points of view. In the first place, the role of such compounds is to act at the very first appearance of the symptoms of thromboses in such a manner as to avoid the appearance thereof at the level of the damaged vascular endothelium. It is imperative that, in contradistinction to anti-coagulants, the anti-aggregants do not modify the aptitude to coagulation (in particular the speed of formation of fibrin) so as to be able to administer concurrently an anti-aggregant and an anti-coagulant in the prophylactic treatment of thrombo-embolisms.

The tendency of platelets to aggregate in the human plasma increases with age as well as in subjects who suffer from vascular diseases, including chronic arterial obstructions and venous obstructions. Similarly, in the case of subjects who do not suffer from vascular diseases, the tendency for platelets to aggregate increases after infections. The anti-coagulant compounds (for example phenprocoumon or heparin) as a rule have an influence on the fibrin formation phase without remedying the increase of the tendency of platelets to aggregate. It is for this reason that intensive research has been carried out recently in order to discover medicaments which do not have any action on the mechanism of hemostasis but which diminish or suppress platelet aggregation. For example, acetylsalicylic acid has been found to have an important action not only on platelet aggregation but, unfortunately, also on hemostasis, which limits its therapeutic utility in this field.

The same applies to other anti-aggregant compounds, such as indomethacin and phenylbutazone, which have an undesirable influence on the effective dose of indirect anti-coagulants, for example phenprocoumon. This excludes an attempt to carry out a therapy combining these two types of drugs. An ideal anti-aggregant compound must reduce, or even eliminate, the tendency to aggregation without having any secondary effects, especially upon hemostasis. In other words, at the concentration at which these compounds inhibit platelet aggregation, they must not have any other influence on the other platelet factors responsible for the role of platelets in hemostasis. In particular, it is eminently desirable that these drugs do not have any influence on the mechanism of coagulation and, in particular, upon the formation of thrombin. Hitherto, such medicaments are extremely rare (see, for example, E. Wenzel et al., Med. Welt, 25, (1976)).

From this point of view, the action of the compounds of general formula (I) above, namely, piracetam and its two higher homologues, is particularly interesting. These compounds do not modify the distribution of the thrombocytes (platelets) according to their volume nor the morphological parameters of the thrombocytes observed under the microscope, even at high concentrations of the order of $5 \times 10^{-2}$ mol per liter. The three compounds very effectively inhibit an aggregation induced by adenosine diphosphate (ADP) up to concentrations of $10^{-5}$ mol per liter. Furthermore, it is their specificity which is most interesting because, besides inhibiting the aggregation induced by ADP, they do not affect the other platelet functions. Although this effect has been observed for the first time clinically with piracetam in vivo, it appears that this compound, at the same concentration but in vitro, does not seem to be a priori as interesting, especially as compared with compounds B and C. This is bound up with the fact that in vitro tests give an orientation or an idea of the activity of the test compound, without it being possible a priori to transpose these conclusions integrally in vivo.

The following tests serve to demonstrate these conclusions.

A. Presentation of the various methods used

1. Thromboelastographic measurements on citrate plasma rich in platelets

In a TEG apparatus (Hartert's apparatus), a human citrate plasma rich in platelets obtained from healthy subjects is recalcified. In this plasma, the number of thrombocytes and the concentration of fibrinogen are known and constant. Recalcifying is carried out by the use of a 0.1 molar solution of calcium chloride. The role of the citrate is to prevent any coagulation before starting the experiments. Indeed, the citrate ions behave as a chelating agent towards the calcium ions present in the plasma, which are at the origin of the coagulation process. The coagulation process may thus be started at any moment by a simple recalcification on adding calcium chloride. It is to be recalled that this thromboelastographic technique makes use of the increase in viscosity of a blood preparation in the course of coagulation. The principle of this technique consists in subjecting to an oscillating angular movement a cup containing the preparation being investigated and of studying the effects of the coagulation on a cylinder suspended to the extremity of a torsion wire and plunging into the preparation. At the beginning of coagulation, the plasma contained in the cup entrains the cylinder in its oscillating movements. Coagulation time $t = 0$ is the moment at which the activation of the factors responsible for the coagulation is initiated by the addition of calcium ions. Further, $r$ = the latent period which precedes the effective beginning of coagulation, $am$ = the maximum amplitude of the oscillations of the cylinder, $k$ = the time interval from the moment when the cylinder starts oscillating to the moment when the amplitude of movement becomes equal to the maximum amplitude obtained under the same conditions with a plasma without platelets and having a normal fibrinogen content.

The total coagulation time of a preparation is constituted by the sum $r + k$. The kinetics of the coagulation is expressed by the parameters $r$ and $r + k$ and the intensity of the coagulation by the maximum amplitude $am$ of the oscillations of the cylinder.

The equation $am/(r+k)$ expresses the speed of solidification of the coagulum (clot).

In the same manner, there is also measured the maximum elasticity of the thrombus (in the following Tables max. E), which is an indirect measure of the retraction of the fibrin coagulum induced by the thrombocytes. The determination of the maximum ½-lysis time is used in order to show that there is no activation of the fibrinolytic system.

2. Measure of the coagulation

The partial recalcification time of a plasma treated with kaolin (PTT test) is used as a measure of the capacity of the formation of intrinsic prothrombinase (see H. Vinazzer, Gerinnungsstörungen in der Praxis, pub. Fischer Verlag, Stuttgart, 1972). For the speed of formation of extrinsic thrombin, there is used the prothrombin time measurement test (PTZ test) and the hepatoquick test (see Vinazzer, loc. cit.).

The phase of polymerization of the fibrin is studied by the time of coagulation induced by thrombin, reptilase and thrombin-coagulase (see E. Wenzel et al., Dtsch. med. Wsch., 15, (1974), 746–756 and P. E. Gregoire, Biochemie pathologique, pub. Presses Acad. Europeenes, Paris, Maloine, 1972, Chapter 39, p.831 (Les Maladies Hémorragiques).

3. Morphological studies of the thrombocytes and analysis of the distribution of platelets according to their volume The morphology of the thrombocytes, spread on a slide of an interference microscope (enlargement × 400), is used as a very sensitive test for evaluating the functional alteration of the thrombocytes. This test essentially gives non-quantitative indications and, in particular, enables alterations in the energy metabolism of the thrombocytes to be detected.

The volume analysis of the particles with a channel analyzer (Coulter Counter Channelyzer), which is electronic and automatic, enables quantitative but less sensitive data to be obtained for the more pronounced alterations of the thrombocytes. Thus, by this method, the typical morphological alterations of the thrombocytes or the process of fragmentation or also the aggregation phenomena may be precisely determined quantitatively. Smaller modifications are, however, not detected by this test (see H. Holzhüter et al., Thromb. et diath. Suppl., in the press, 1976; see also H. Holzhüter et al., Verh. Dtsch. Ges. f. Inn. Med., 1974).

4. Turbidimetric measurement of the aggregation process

In an aggregometer modified according to Born (ELVI model) or in an Eppendorf universal aggregometer, there is placed, with continuous agitation, a plasma rich in platelets (PRP) at 37° C. After a constant preliminary incubation period of 30 minutes, to the PRP is added ADP ($10^{-4}$ to $10^{-6}$ molar) or collagen (20 μg to 4 μg/ml PRP) and the process of aggregation is directly recorded in the form of curves of decrease of extinction or of increase of transmission. The maximum change of extinction per minute, or the time which, on the extinction curve, separates the first point of inflection from the lowermost point on this curve (the so-called reaction time) are taken as measurement parameters. These measurements are completed by an analysis of the distribution of the non-aggregated thrombocytes according to their volume.

B. Results of the tests

Unless otherwise stated, the concentrations indicated for the compounds A, B and C are the final concentrations in the test samples in moles per liter.

1. Influence of compounds A, B and C on the functional aptitudes of human thrombocytes To a PRP obtained from the plasma of 10 healthy persons, there are added increasing amounts of compounds A, B and C, whereafter the samples are incubated for 30 minutes at ambient temperature after which there are carried out:

an analysis of the volume distribution of the platelets (Coulter Counter);
thromboelastographic tests in a recalcified PRP;
morphological examination of the thrombocytes, spread on a microscope slide.

Results and conclusions

Even high concentrations (1 mol) of compounds A and C only have a very minimum influence on the morphology of the spread thrombocytes (slight increase of the unspread thrombocyte forms). At concentrations of $10^{-2}$ mol or less, this effect is no longer detectable for any of the compounds A, B or C. The results obtained are given in the following Table I (the normal value for unspread thrombocytes lies between 35 and 45%).

TABLE I

| Compound (mol) | Evaluation | % unspread thrombocytes |
|---|---|---|
| blank I (NaCl) | slight inhibition | 39 |
| blank II (NaCl) | slight inhibition | 41 |
| A 1 | slight increase of inhibition | 43 |
| A $10^{-1}$ | as blank | 38 |
| A $10^{-2}$ | as blank | 40 |
| A $10^{-3}$ | as blank | 37 |
| B 1 | as blank | 39 |
| B $10^{-1}$ | as blank | 40 |
| B $10^{-2}$ | as blank | 37 |
| B $10^{-3}$ | as blank | 40 |
| C 1 | slight increase of inhibition | 41 |
| C $10^{-1}$ | as blank | 39 |
| C $10^{-2}$ | as blank | 40 |
| C $10^{-3}$ | as blank | 39 |

The distribution of the thrombocytes according to their volume is not modified, not even by high concentrations of the three compounds tested.

The following Table II indicates the number of thrombocytes at increasing concentrations of compounds A, B and C.

TABLE II

| Compound (mol) | number of thrombocytes |
|---|---|
| Blank | 95,000 |
| A $10^{-1}$ | 107,000 |
| $10^{-2}$ | 98,000 |
| $10^{-3}$ | 97,000 |
| B $10^{-1}$ | 97,000 |
| $10^{-2}$ | 98,000 |
| $10^{-3}$ | 97,000 |
| C $10^{-1}$ | 95,000 |
| $10^{-2}$ | 94,000 |
| $10^{-3}$ | 89,000 |

Furthermore, the functional thromboelastographic parameters of the platelets and, in particular, the maximum solidity of the thrombus (which is an indirect measure of the retraction of the coagulum under the effect of the thrombocytes) is not significantly influenced by even high concentrations of compounds A, B or C. In the following Table III, there are given the results of the thromboelastogram, measured on solutions containing 9 parts of PRP and 1 part of test compound.

TABLE III

| Compound (mol) | r | k | r + k | am | am/(r + k) | max.E |
|---|---|---|---|---|---|---|
| blank PRP | 1.6 | 0.5 | 2.1 | 4.9 | 2.33 | 96.1 |
| blank NaCl | 2.0 | 0.8 | 2.8 | 5.4 | 1.93 | 117.4 |
| A $10^{-3}$ | 1.5 | 0.5 | 2.0 | 4.7 | 2.35 | 88.7 |
| $10^{-4}$ | 1.7 | 1.1 | 2.8 | 3.3 | 1.18 | 49.3 |
| $10^{-5}$ | 1.5 | 1.1 | 2.6 | 3.0 | 1.15 | 42.9 |
| blank PRP | 1.6 | 0.5 | 2.1 | 4.9 | 2.33 | 96.1 |
| blank NaCl | 2.0 | 0.8 | 2.8 | 5.4 | 1.93 | 117.4 |
| B $10^{-3}$ | 1.9 | 0.8 | 2.7 | 6.0 | 2.22 | 150.0 |
| $10^{-4}$ | 2.3 | 1.2 | 3.5 | 4.9 | 1.4 | 96.1 |
| $10^{-5}$ | 1.4 | 0.4 | 1.8 | 6.0 | 3.3 | 150.0 |
| blank PRP | 6.4 | 3.0 | 9.4 | 4.7 | 0.5 | 88.7 |
| blank NaCl | 6.5 | 2.4 | 8.9 | 5.6 | 0.63 | 127.3 |
| C $10^{-3}$ | 5.8 | 2.2 | 8.0 | 4.6 | 0.58 | 85.2 |
| $10^{-4}$ | 5.0 | 3.7 | 8.7 | 3.9 | 0.45 | 63.9 |
| $10^{-5}$ | 4.1 | 1.4 | 5.5 | 4.5 | 0.82 | 82.2 |

Table III shows the influence of compounds A, B and C on the maximum solidity of the thrombus and on the time of formation of the coagulum by the thromboelastographic tests on a human PRP before and after the addition of the test compounds. Final concentrations of $10^{-2}$ to $10^{-5}$ mol of these compounds influence the maximum solidity of the thrombus and the time of formation of the coagulum only to a very minor degree.

2. Influence of high concentrations of compounds A, B and C on the formation of intrinsic and extrinsic thrombin and on the rate of polymerization of the fibrin To a plasma obtained from healthy donors, there are added increasing concentrations of the test compounds, then the samples are incubated at ambient temperature for 30 minutes. As a blank, there are used the same plasmas to which there is added the same volume of the solvent which is used for the test compounds (9 parts of isotonic sodium chloride solution per one part of citrate). The pH values of the solutions thus obtained vary between 7.2 and 7.6.

Results and conclusions

Even high concentrations of the three test compounds (up to $10^{-1}$ mol) do not have any influence on the speed of formation of the intrinsic thrombin (PTT test) and of extrinsic thrombin (Quick-test).

Concentrations higher than $10^{-2}$ mol of the three test compounds have a very distinct inhibiting action on the polymerization of fibrin. However, the thrombin time is only very slightly influenced.

For concentrations equal to or below $10^{-2}$ mol (for example $10^{-2}$ and $10^{-3}$ mol), neither the polymerization of fibrin nor the thrombin formation phase are influenced to any notable extent.

The results of these tests are given in the following Table IV.

TABLE IV

| Compound (mol) | thrombin time | PTT | Quick | fibrinogen | reptilase | thrombin coagulase |
|---|---|---|---|---|---|---|
| blank I (NaCl) | 17.8 | 35.5 | 100 | 168 | 16.8 | 20.3 |
| A $10^{-1}$ | 22.9 | 36.1 | 90 | 144 | 34.1 | 54.0 |
| $10^{-2}$ | 19.0 | 34.6 | 89 | 132 | 18.4 | 21.4 |
| $10^{-3}$ | 20.2* | 32.0* | 100* | 210* | 15.8* | 24.8* |
| blank II (NaCl) | 20.8* | 31.8* | 100* | 240* | 15.0* | 26.5* |
| blank I (NaCl) | 17.8 | 35.5 | 100 | 168 | 16.8 | 20.3 |
| B $10^{-1}$ | 24.9 | 38.5 | 85 | 144 | 37.3 | 42.8 |
| $10^{-2}$ | 18.3 | 34.5 | 89 | 140 | 17.6 | 22.6 |
| $10^{-3}$ | 21.1* | 31.8* | 100* | 240* | 16.5* | 25.6* |
| blank II (NaCl) | 20.8* | 31.8* | 100* | 240* | 15.0* | 26.5* |
| blank I (NaCl) | 17.8 | 35.5 | 100 | 168 | 16.8 | 20.3 |
| C $10^{-1}$ | 22.9 | 36.1 | 90 | 144 | 34.1 | 54.0 |
| $10^{-2}$ | 19.0 | 34.6 | 89 | 132 | 18.4 | 21.4 |
| $10^{-3}$ | 20.2* | 32.0* | 100* | 210* | 15.8* | 24.8* |
| blank II (NaCl) | 20.8* | 31.8* | 100* | 240* | 15.0* | 26.5* |

*The asterisk indicates that blank II corresponds to the tests carried out at the concentration of $10^{-3}$ mol. These results are expressed in seconds except for fibrinogen where they are expressed in mg/100 ml.

3. Influence of compounds A, B and C on platelet aggregation induced by collagen or ADP The influence of increasing concentrations of compounds A, B and C on platelet aggregation induced by high and low concentrations of ADP or collagen is studied quantitatively. PRP is incubated for 30 minutes with the substances tested up to concentrations of the order of $10^{-5}$ mol. As a blank, there is used PRP with a constant number of thrombocytes, either as such or with the addition of a buffer. Each test lasts about 4 hours and one must bear in mind the alteration of the platelets which takes place in any case when human thrombocytes are left at ambient temperature (there is indeed a spontaneous tendency thereof to aggregate). Consequently, all the blanks are repeated after each series of tests.

In the first preliminary tests, there is used the turbidimetric method modified according to Born's principle (ELVI turbidimeter). As a measure of the aggregation (or deaggregation), there is used the extinction change measured by graphic extrapolation of the recorded extinction curve. In addition to this, there is also taken into consideration the slope of the curve and the maximum transmission change during the course of the reaction.

The quantitative measurement of the aggregation and deaggregation phenomena is evaluated by the decrease in the absolute number of platelets (decrease in the number of non-aggregated thrombocytes in the plasma after the aggregation process). On the other hand, there is recorded the volumetric distribution of the free platelets, which are not aggregated, during the aggregation process. There is thus obtained a direct measurement of the aggregation kinetics and of the deaggregation process.

For the aggregation experiments induced by ADP or collagen, there are used plasmas for healthy subjects which contain, on average, between 80,000 and 120,000 platelets/mm$^3$. All the experiments were repeated several times.

Results

Compounds A, B and C inhibit platelet aggregation induced by ADP or by collagen, without having an effect on the distribution of the thrombocytes according to their volume. Indeed, on the contrary, the influence of ADP and of collagen on this latter is suppressed (this influence manifests itself by a decrease of the bigger thrombocytes which are particularly functionally active and by a relative increase of the number of smaller thrombocytes, which are relatively less active, always speaking functionally).

For compound A, this is demonstrated, in the first place, with photometric methods.

In the following Table V, there are given the results of extinction curves (but not the curves themselves). Aggregation is induced by ADP at different concentrations ($10^{-4}$, $10^{-5}$ and $10^{-6}$ molar). Compound A (0.14 molar) is incubated with the PRP for 30 minutes.

In the following Table, the symbols have the following meanings:

Tr = the time which, on the extinction curve, separates the first point of inflection from the lowermost point on this curve;

Lz = the angle giving a measure of the maximum speed of aggregation;

Max E = the absolute extinction difference in the plasma, before and after aggregation.

TABLE V

| final molar concentration of ADP | compound (mol) | Tr | Lz | Max.E | Number of thrombocytes before aggregation | Number of thrombocytes after aggregation |
|---|---|---|---|---|---|---|
| | NaCl (blank) | 0.5 | 70° | 610 | 112,000 | 20,000 |
| $10^{-4}$ | A 0.14 | 1.0 | 60° | 340 | 109,000 | 78,000 |
| | NaCl (blank) | 0.9 | 71° | 470 | 107,000 | 59,000 |
| $10^{-5}$ | A 0.14 | 1.3 | 31° | 115 | 101,000 | 79,000 |
| $10^{-6}$ | NaCl (blank) | 1.5 | 33° | 220 | 112,000 | 54,000 |
| | A — | | 0° | 95 | 105,000 | 83,000 |

Table VI gives the results of the extinction curves but this time the concentration of compound A is varied. The operating conditions are the same as above. The ADP is used at a concentration of $10^{-6}$ mol per liter. The nondiluted solution of compound A is 1.41 molar.

TABLE VI

| test solutions | final concentration of A (mol) | Tr | Lz | Max.E | Number of thrombocytes before aggregation |
|---|---|---|---|---|---|
| 9 parts PRP + 1 part NaCl | — | 0.9 | 62° | 370 | 152,000 |
| 9 parts PRP + 1 part A (1:0) | 0.14 | — | 180° | 140 | 152,000 |
| 9 parts PRP + 1 part A (1:5) | 0.028 | 1.0 | 45° | 270 | 152,000 |
| 9 parts PRP + 1 part A (1:10) | 0.014 | 1.2 | 59° | 380 | 160,000 |
| 9 parts PRP + 1 part A (1:100) | 0.0014 | 1.0 | 57° | 350 | 160,000 |
| 9 parts PRP + 1 part A (1:1000) | 0.00014 | 1.0 | 58° | 370 | 160,000 |

In the accompanying drawings, there is also given an example of platelets volume distribution curves obtained with compound A under the following conditions:

0.9 ml PRP, incubated for 30 minutes with compound A (0.14 molar);

0.1 ml of a $10^{-4}$ molar solution of ADP.

FIG. I represents the platelets volume distribution curve on using compound A before aggregation, while FIG. II represents the same curve after aggregation.

FIGS. III and IV represent the corresponding curves obtained with a blank (sodium chloride).

The abscissae of the curves give the channels of 0 to 100 (according to the principle of the channel analyser) and the ordinates the number of thrombocytes corresponding to a given channel.

Table VII below gives the results obtained on the photometric curves and on the platelets volume distribution curves for compounds A, B and C. The operating conditions are as follows:

aggregation induced by 0.1 ml of $10^{-6}$ molar solution of ADP;

0.9 ml PRP, incubated for 30 minutes with the test compound.

TABLE VII

| Product final molar concentration | Tr | Lz | Max E 1st summit | Max E 2nd summit | Number of thrombocytes before aggr. | Number of thrombocytes after aggr. | Peak before aggr. | Peak after aggr. |
|---|---|---|---|---|---|---|---|---|
| blank NaCl | 0.9 | 66° | 420 | 730 | 95,000 | 58,000 | 19 | 14 |
| A $10^{-1}$ | — | 0° | 220 | 200 | 107,000 | 76,000 | 19 | 17 |
| A $10^{-2}$ | 0.9 | 62° | 290 | 340 | 98,000 | 37,000 | 17 | 15 |
| A $10^{-3}$ | 0.9 | 62° | 270 | 300 | 97,000 | 27,000 | 18 | 13 |
| B $10^{-1}$ | — | 0° | 80 | 70 | 97,000 | 78,000 | 17 | 16 |
| B $10^{-2}$ | 0.9 | 64° | 380 | 260 | 98,000 | 50,000 | 15–20 | 15 |
| B $10^{-3}$ | 0.8 | 66° | 450 | 500 | 97,000 | 26,000 | 16 | 5 |

TABLE VII-continued

| Product final molar concentration | Tr | Lz | Max E 1st summit | Max E 2nd summit | Number of thrombocytes before aggr. | Number of thrombocytes after aggr. | Peak before aggr. | Peak after aggr. |
|---|---|---|---|---|---|---|---|---|
| C $10^{-1}$ | — | 0° | 80 | 80 | 95,000 | 84,000 | 17 | 15 17 |
| C $10^{-2}$ | 1.1 | 66° | 390 | 290 | 94,000 | 55,000 | 17 | 15 |
| C $10^{-3}$ | 1.4 | 70° | 420 | 400 | 89,000 | 30,000 | 16 | |
| blank NaCl | 0.9 | 65° | 500 | 760 | 98,000 | 11,000 | 19 | 15 5 |

The same experiments were carried out for aggregations induced by different concentrations of collagen. In Table VIII (concentration of collagen 4 μg/ml) and Table IX (concentration of collagen 20 μg/ml) given hereinafter, there are given the results obtained on the photometric curves and on the platelets volume distribution curves using compounds A, B and C. The operating conditions are as follows:

aggregation induced by collagen at the rate of 20 and 4 μg of collagen (in suspension) per ml of PRP;
0.9 ml of PRP incubated for 30 minutes with the test compound.

TABLE VIII

| test compound (mol) | Tr | Lz | Max.E | Number of thrombocytes before aggr. | Number of thrombocytes after aggr. | Peak before aggr. | Peak after aggr. |
|---|---|---|---|---|---|---|---|
| blank (NaCl) | 7.5 | 80° | 820 | 106,000 | 4,000 | 14 | 3 |
| A $10^{-2}$ | 6.4 | 79° | 700 | 106,000 | 4,000 | 14 | 3 |
| B $10^{-3}$ | 6.2 | 80° | 790 | 106,000 | 10,000 | 14 | 3 |
| $10^{-4}$ | 7.3 | 78° | 820 | 106,000 | 5,000 | 14 | 3 |
| C $10^{-3}$ | 7.0 | 78° | 790 | 106,000 | 5,000 | 14 | 3 |

TABLE IX

| test compound (mol) | Tr | Lz | Max.E | Number of thrombocytes before aggr. | Number of thrombocytes after aggr. | Peak before aggr. | Peak after aggr. |
|---|---|---|---|---|---|---|---|
| blank (NaCl) | 4.0 | 82° | 1060 | 111,000 | 5,000 | 13 | 3 |
| A $10^{-1}$ | 8.0 | 74° | 790 | 106,000 | 18,000 | 14 | 11 |
| 10 $10^{-2}$ | 6.4 | 79° | 860 | 106,000 | 4,000 | 14 | 3 |
| B $10^{-1}$ | 7.5 | 70° | 630 | 106,000 | 33,000 | 14 | 12 |
| $10^{-2}$ | 4.3 | 77° | 990 | 106,000 | 4,000 | 14 | 3 |
| C $10^{-1}$ | 8.0 | 0° | 340 | 106,000 | 78,000 | 14 | 11 |
| $10^{-2}$ | 5.1 | 81° | 900 | 106,000 | 4,000 | 14 | 3 |

Table IX shows that the three compounds A, B and C, at a final concentration of $10^{-1}$ mol, inhibit the aggregation induced by 20 μg of collagen. The descending order of activity of the compounds is C, B, A, not only in the optical measurements but also in the measurement of the thrombocyte count. At $10^{-2}$ mol the activity is not observable. Table VIII shows, on the other hand, insofar as it concerns the aggregation induced by a smaller quantity of collagen (4 μg), that only compound B is active in a dosage equal to $10^{-3}$ mol or even $10^{-4}$ mol.

From what has been stated hereinbefore, it can be seen that, especially in the case of aggregation induced by ADP, the three compounds appear to be equally active. The measurements made with collagen appear to indicate, however, the superiority of B and C over A. The examination of the form of the aggregation curves also shows an increase of the speed of deaggregation.

The general conclusion which can be drawn from these tests is that, leaving concentration considerations aside, the three compounds have a very similar type of action: they diminish, in a particularly effective manner, the aggregation of platelets induced by ADP and increase the speed of deaggregation during the phenomenon of the ADP aggregation. They also protect the platelets against the morphological modifications induced by ADP or by collagen. Thus, the "platelets anti-aggregant" activity of these compounds appears to be very interesting. This is all the more so, considering that this activity is not simultaneously accompanied by an undesirable influence on the mechanism of coagulation and, in particular, upon the formation of thrombin.

A comparison of the activity of compound C with that of a known anti-aggregant, namely lysine acetylsalicylate, sold under the Trade Mark "Aspisol" and designated hereinafter by "compound X", shows the medical interest of the first compound (as well as that of its homologues: compounds B and A).

Compound X, in fact, has superior antiaggregant properties, as can be seen from Table X below giving the results of the aggregation test induced by collagen.

TABLE X

| Compound (mg/ml) | Maximum speed of aggregation Lz | Maximum extinction Max.E | Aggregation latency | Interpretation |
|---|---|---|---|---|
| Blank | 51° | 320 | 27 | normal |
| C (2) | 61° | 390 | 39 | normal type of aggregation, but delayed |
| (4) | 51° | 400 | 52 | |
| X (2) | 24° | 200 | 64 | slowed down speed, reduced intensity, very marked delay |
| (4) | 0 | 0 | ∞ | total inhibition |

It can be seen that, under the prevailing conditions, compound C slightly delays aggregation in proportion to the concentration used. This delay is interpreted as a slight inhibition. Compound X inhibits agregation partially at 2 mg/ml, but completely at 4 mg/ml.

However, unlike compound C, compound X has two secondary effects, which might be harmful:

1. Table XI, giving the comparative results of thromboelastography, shows that compound X slows down the formation of the coagulum because of its anticoagulant properties, this effect being proportional to the concentration used. On the contrary, compound C does not show this particularity.

TABLE XI

| Compound (mg/ml) | Time for the formation of the coagulum r + k | Interpretation |
|---|---|---|
| C (2) | 2.8 | normal |
| (4) | 2.3 | normal |
| X (2) | 4.6 | marked slowing down of the speed of coagulation |
| (4) | 5.2 | |

2. Tables XII and XIII, which give the distribution of the platelets according to their volume, respectively before and after the addition of collagen, show that, whereas compound C leaves this distribution practically unchanged, compound X, on the contrary, produces an increase of the percentages of the smaller platelets, which are functionally less active (smaller contracted platelets and cellular fragments).

TABLE XII (before addition of collagen)
Percentages of platelets measured among the following volumes:

| Compound (mg/ml) | 0 to 2.16 $\mu^3$ | 2.16 to 4.56 $\mu^3$ | 4.56 to 6.9 $\mu^3$ | 6.9 to 9.36 $\mu^3$ | 9.36 to 11.76 $\mu^3$ | 11.76 to 14.16 $\mu^3$ | 14.16 to 16.56 $\mu^3$ | 16.56 to 19.96 $\mu^3$ | Interpretation |
|---|---|---|---|---|---|---|---|---|---|
| Blank | 2.6 | 11.04 | 21.82 | 21.50 | 16.19 | 10.59 | 6.73 | 4.42 | normal |
| C (2) | 4.35 | 15.13 | <u>24.0</u> | 20.7 | 13.7 | 8.8 | 5.6 | 3.75 | normal |
| (4) | 6.14 | 14.4 | <u>23.7</u> | 21.0 | 14.0 | 8.6 | 5.3 | 3.5 | normal |
| X (2) | 5.3 | 15.9 | <u>24.3</u> | 20.7 | 13.8 | 8.3 | 5.0 | 3.2 | normal |
| (4) | 6.4 | 16.6 | <u>25.65</u> | 20.94 | 13.21 | 7.6 | 4.3 | 2.7 | normal | underlined = maximum

TABLE XIII (after addition of collagen)
Percentages of platelets measured among the following volumes:

| Compound (mg/ml) | 0 to 2.16 $\mu^3$ | 2.16 to 4.56 $\mu^3$ | 4.56 to 6.96 $\mu^3$ | 6.96 to 9.36 $\mu^3$ | 9.36 to 11.76 $\mu^3$ | 11.76 to 14.16 $\mu^3$ | 14.16 to 16.56 $\mu^3$ | 16.56 to 18.96 $\mu^3$ | 18.96 to 21.36 $\mu^3$ | 21.36 to 23.76 $\mu^3$ | Interpretation |
|---|---|---|---|---|---|---|---|---|---|---|---|
| Blank | 2.6 | 11.0 | 21.8 | 21.5 | 16.2 | 10.6 | 6.7 | 4.4 | 2.9 | 1.8 | (1) |
| C (2) | 4 | 14.1 | <u>23.4</u> | 21.1 | 14.4 | 9.1 | 5.9 | 3.9 | 2.6 | 1.6 | (2) |
| (4) | 6 | 15.6 | <u>23.8</u> | 20.1 | 13.5 | 8.3 | 5.4 | 2.3 | 1.53 | — | (2) |
| X (2) | 21.7 | <u>26.1</u> | 22.7 | 13.2 | 7.0 | 3.9 | 2.4 | 1.3 | 1 | 0.7 | (3) |
| (4) | <u>50.1</u> | 22.4 | 12.9 | 6.5 | 3.4 | 2.15 | 1.13 | 0.72 | 0.45 | 0.24 | (4) | underlined = maximum
(1) normal distribution without collagen = blank
(2) normal
(3) mixed distribution: cellular fragments - platelets
(4) characteristic distribution of cellular fragments. Very few whole platelets Consequently, compound C (as well as compounds B and A) will avantageously replace compound X in all cases where the latter drug might be a contra-indication and more particularly in the following situations:
(a) gastro-duodenal ulcers or persons having had such antecedants;
(b) any surgical operation and in particular vascular or cardiac arterial reconstruction surgery, for instance open heart operations;
(c) thrombogenic diseases in general (cardiac, cerebral, limbs);
(d) general platelet pathology (thromboasthenia, thrombopenia, thrombocythemia).

C. Posology

The experiments concerning the metabolism of compounds A, B and C have shown that a dosage of 8.5 to 500 mg/kg administered three times a day at 8 hour intervals enables a blood level to be obtained which is sufficient to inhibit platelet aggregation in vivo.

D. Type of administration

The intensity and speed of resorption of these compounds enables the desired blood levels to be obtained whatever the route of administration may be (per os, intramuscular, intraperitoneal or intravenous).

E. Galenical forms

Examples of appropriate galenical forms include the following:
administration per os: gelatine capsules containing 500 mg of active material;
intramuscular or intraperitoneal administration: ampoules containing 1 g of active material in 5 ml of double distilled water;
drinkable soution: 100 mg of active material per ml water + propylene glycol.

F. Indications

Compounds A, B and C can be used for the following indications: mycocardial infarcts resulting from platelet hyperaggregability or hyperadhesivity, extracorporeal circulation or the use of valve prostheses, thromboembolic diseases and hyperaggregability in coronary patients.

I claim:

1. A process of inhibiting blood platelet aggregation, which comprises administering internally to a man requiring such inhibition an amount effective to inhibit platelet aggregation of a 2-(2-oxo-pyrrolidino)alkanamide having the formula

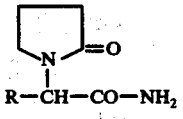

wherein R is a hydrogen atom or a methyl or ethyl radical.

2. The process of claim 1, wherein the administration is oral, intramuscular, intraperitoneal or intravenous.

3. The process of claim 1, wherein the amount effective to inhibit platelet aggregation is from 8.5 to 500 mg/kg administered three times a day at 8 hour intervals.

4. The process of claim 1, wherein said 2-(2-oxo-pyrrolidino)alkanamide is 2-oxo-1-pyrrolidineacetamide.

5. The process of claim 1, wherein said 2-(2-oxo-pyrrolidino)alkanamide is 2-(2-oxo-pyrrolidino)-propionamide.

6. The process of claim 1, wherein said 2-(2-oxo-pyrrolidino)alkanamide is 2-(2-oxo-pyrrolidino)-butyramide.